(12) United States Patent
Camus et al.

(10) Patent No.: US 7,778,453 B2
(45) Date of Patent: Aug. 17, 2010

(54) MULTI-MODALITY METHOD AND SOFTWARE FOR REPRESENTATION AND EVALUATION OF EXTREMITY EXPOSURES OF ARTHRITIS/ARTHROSIS PATIENTS

(75) Inventors: Estelle Camus, Erlangen (DE); Oliver Meissner, München (DE)

(73) Assignee: Siemens Aktiengesellschaft, Munich (DE)

( * ) Notice: Subject to any disclaimer, the term of this patent is extended or adjusted under 35 U.S.C. 154(b) by 820 days.

(21) Appl. No.: 11/668,566

(22) Filed: Jan. 30, 2007

(65) Prior Publication Data
US 2008/0181470 A1    Jul. 31, 2008

(51) Int. Cl.
G06K 9/00    (2006.01)
(52) U.S. Cl. .................. 382/128; 382/130; 382/132; 382/281
(58) Field of Classification Search .......... 382/128, 382/130, 132, 218; 600/407; 607/72; 424/9.5
See application file for complete search history.

(56) References Cited

U.S. PATENT DOCUMENTS 7,187,790 B2 *  3/2007  Sabol et al. .................. 382/128
7,664,297 B2 *  2/2010  Harada et al. ............... 382/128

\* cited by examiner

*Primary Examiner*—Anh Hong Do
(74) *Attorney, Agent, or Firm*—Schiff Hardin LLP (57)    ABSTRACT

In a multi-modality method for representing functional and morphological exposures of an extremity of patients exhibiting arthritis/arthrosis, and corresponding computer software, images obtained with different imaging modalities are supplied to a computer and displayed at the computer with a default line model of the extremity superimposed on each of the images. A user interacts with the computer to modify the line model as necessary, so that each of the images has a modified line model associated therewith. The images obtained from the different imaging modalities are then superimposed and registered with each other by conforming the respective modified line models with each other. One of the images can be composed of a number of sub-images, obtained at respective joints in the extremity. These individual images of the joint can be fused with the image of the complete extremity, so that in a display of such a fused image, the individual joint images can be selected and displayed.

22 Claims, 7 Drawing Sheets

MULTI-MODALITY METHOD AND SOFTWARE FOR REPRESENTATION AND EVALUATION OF EXTREMITY EXPOSURES OF ARTHRITIS/ARTHROSIS PATIENTS

BACKGROUND OF THE INVENTION

1. Field of the Invention

The present invention concerns a method and software for obtaining an early diagnosis of arthritis/arthrosis in patients.

2. Description of the Prior Art

Degenerative or inflammatory diseases of the musculoskeletal system represent a significant socioeconomic challenge. Due to the increasing aging of a large segment of society, it is expected that arthrotic diseases will substantially increase within the next few years. Diseases in the rheumatic group such as primary chronic polyarthritis (PcP, rheumatoid arthritis) which represents the most frequent inflammatory rheumatic illness, also exhibit an increased incidence. Rheumatoid arthritis is not a disease that is exclusively associated with elderly persons. Rather, the disease generally begins between the $30^{th}$ and $40^{th}$ year of life, with a predilection for occurrence in younger women. "Juvenile arthritis" is a special form of this illness that already begins between the third and eighteenth year of life. New pharmaceutical therapy techniques are directed toward treating early forms of inflammatory and degenerative illnesses of the musculoskeletal system as early as possible. The goal is to avoid, or to retard as long as possible, late forms that are usually associated with a significant limitation in the movement capabilities of the patient, as well as an enlargement of joints that is visibly apparent.

Both for degenerative and inflammatory diseases of the anatomy involved in movement, early forms of these diseases are often very difficult to diagnose. The same is true for assessing the success of an early treatment. Moreover, particularly with the early forms of such illnesses, there is a high degree of overlap in the symptoms of inflammatory and degenerative diseases, so that association of a specific disease profile with a specific therapy regimen is not always possible.

In addition to clinical examination and laboratory chemical analysis, medical imaging plays a decisive role in the diagnosis and assessment of a treatment regimen for inflammatory and degenerative diseases of the musculoskeletal system. Conventional x-ray imaging and/or functional imaging techniques, such as ultrasound and nuclear medicine, are among the conventionally used techniques. Magnetic resonance tomography additionally provides an imaging modality that can encompass both morphological and functional parameters in an ideal manner. Due to the relatively high costs associated therewith, and the fact that magnetic resonance tomography systems are not as commonplace as x-ray imaging systems, magnetic resonance tomography has only seldom been used in the diagnosis of early forms of arthritis/arthrosis.

In addition to imaging clinically conspicuous (suspicious) joints, imaging of one or both hands and/or one or both feet (i.e., the extremities of a patient) is primarily implemented for the diagnosis of arthrotic/arthritic illnesses, since early stages of both of these illnesses are manifested in the extremities.

A basic problem of the use of conventional x-ray diagnostics in this context is that the early phase of these diseases produces only indirect signs in an x-ray image, such as a widening (expansion) of the soft tissue shadow, a joint-proximal, band-shaped demineralization, or a widening, followed by subsequent narrowing, of the joint spaces. These features can be detected only with difficulty in a conventional x-ray image.

A further problem in standardizing diagnostics in this field is that different examination modalities may be implemented by different examiners (physicians). All examiners do not always have access to all modalities. Moreover, examinations often occur in different departments of a clinic or hospital, thereby necessitating that the different results from different departments be collected and evaluated in common. Additionally, not all examination modalities are DICOM-compatible, and therefore the results thereof cannot be displayed at a viewing station. Lastly, there are frequently no standardized examination or parameter conditions, making it difficult to compare one examination result with another.

SUMMARY OF THE INVENTION

It is an object of the present invention to provide an image processing method and system that allows morphological and functional modalities to be registered, superimposed and evaluated together, in the context of diagnosing arthritis/arthrosis.

In a first embodiment of the inventive method and system, the above object is achieved by acquiring a number of exposures of an extremity of a patient, such as the patient's hand or foot, with different imaging modalities. One of these exposures is automatically uploaded into an evaluation program running at a workstation, such as a PACS. The evaluation program provides the viewer with a line representation or line sample of the extremity and, by interaction with an interface at the workstation, the user/viewer semi-automatically adapts the line representation to the displayed exposure. When the adaptation is completed to the user's satisfaction, the user enters a confirmation and the program automatically undertakes a calculation that transforms a default line representation into the adapted line representation.

These steps are implemented for each exposure obtained with the different modalities.

When all of the transformations for all of the exposures required with the different modalities have been calculated, all of the images (exposures) can be registered together and superimposed, possibly with suitable scaling. By interaction via an interface with the displayed superimposed images, the user can select colors, select the degree of transparency of the colors, bring a selected image to the foreground, etc. in order to enhance the display of the superimposed images according to the user's preference and experience. The superimposed images are then stored.

In a further embodiment of the inventive method and system, ultrasound exposures, such as static images and/or cine loops, of joints of an extremity, such as the hand or foot of a patient, are registered together with images of the entire extremity obtained with different imaging modalities. Each ultrasound image is provided with an anatomical designation in the DICOM header thereof. On a PACS or a workstation, the images of the entire extremity are uploaded and an evaluation program similar to that described above is initiated. A line representation or line sample of the extremity is generated and adapted by the user, via an interface with the workstation, with the user entering indications with the same anatomical designations as the ultrasound exposures. The program automatically generates a concordance list between the adapted line representation and the ultrasound exposures.

When the user subsequently undertakes a medical evaluation of one of the entire extremity images obtained with one of the imaging modalities, the user can interact via an interface with the displayed image so as to make a mouse click on a particular joint. The corresponding ultrasound exposure or exposures for that joint are thereby automatically uploaded and displayed.

DESCRIPTION OF THE PREFERRED EMBODIMENTS

Figure 1:
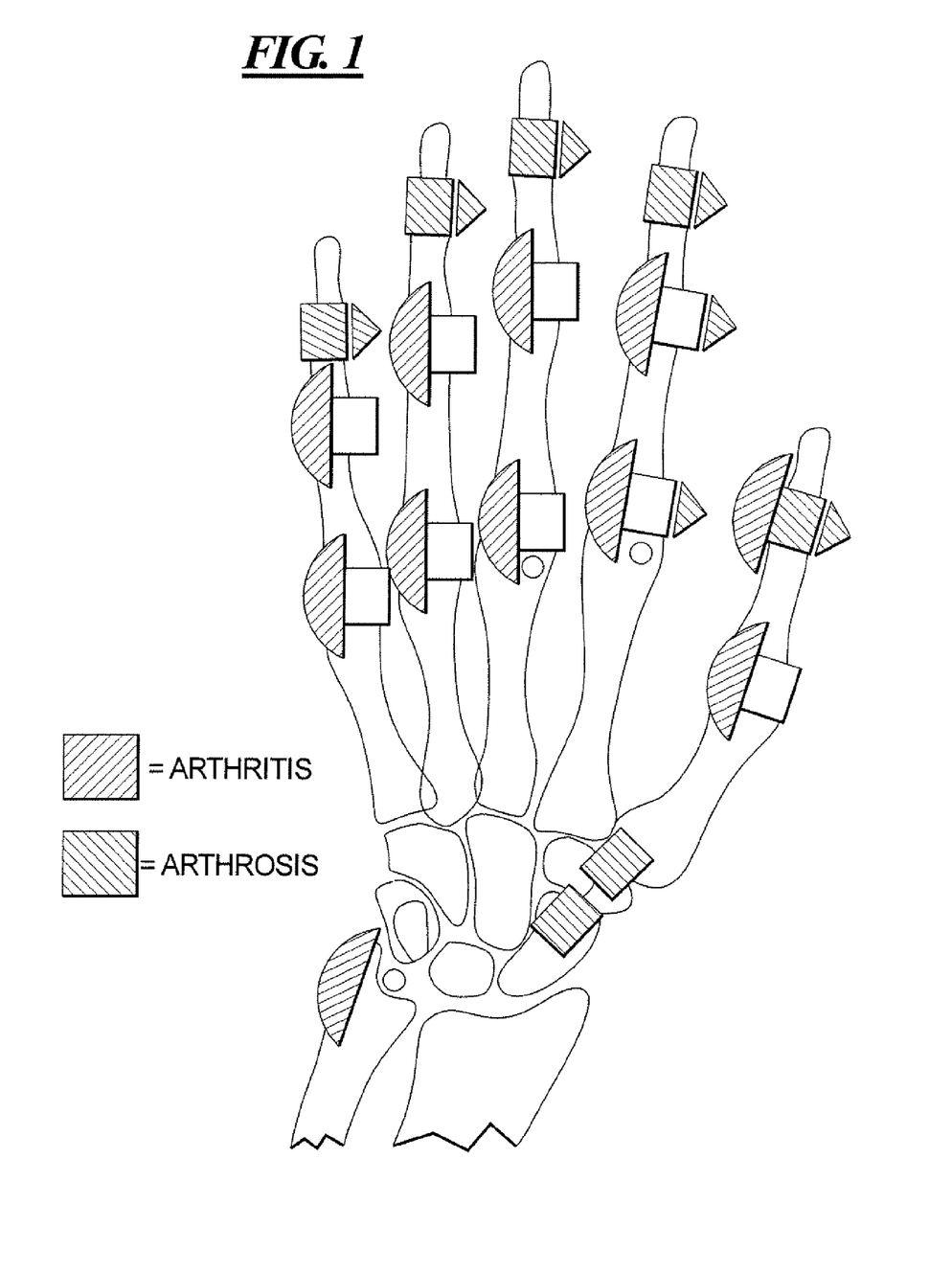
FIG. 1 schematically illustrates typical sites of manifestation of arthritis/arthrosis in the joints of an extremity, shown in the example of a hand of a patient.

FIG. 1 schematically illustrates typical sites of the manifestation of arthritis/arthrosis in the joints of an extremity, shown in the example of a hand of a patient. The arthritis and arthrosis sites are respectively indicated by the differently hatched areas.

Figure 2:
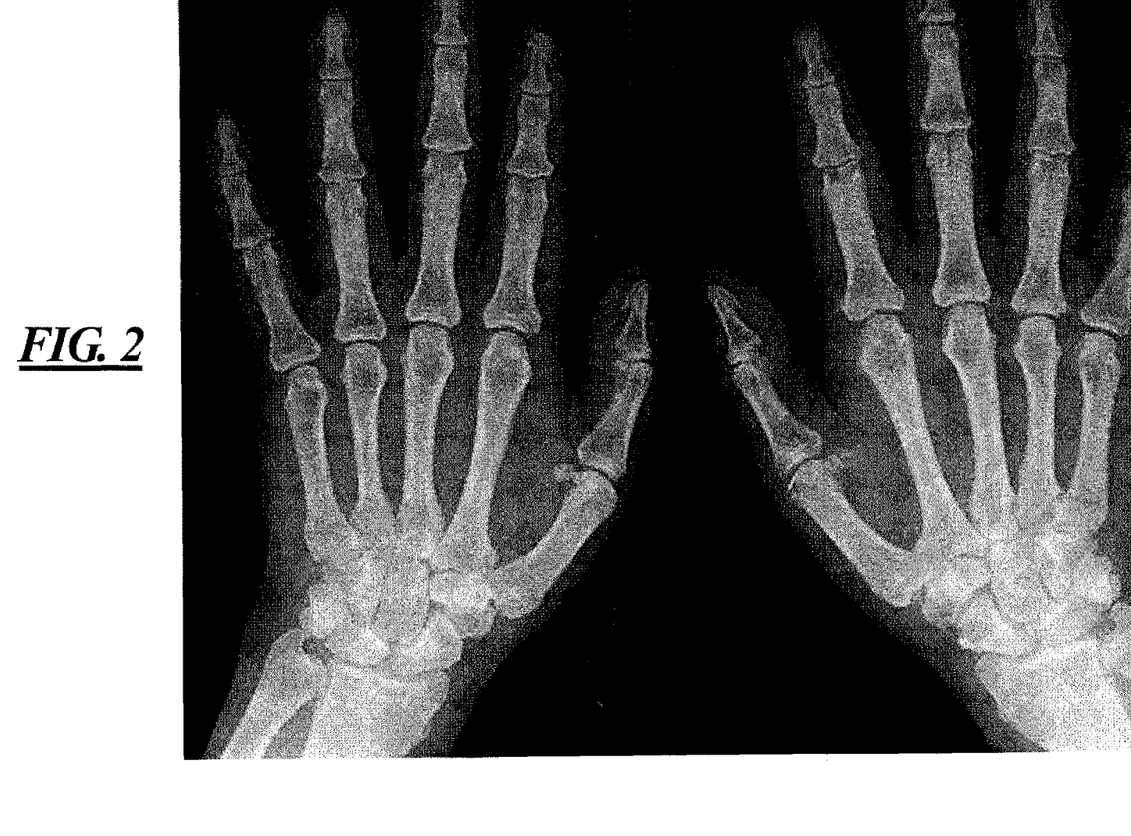
FIG. 2 is an x-ray of a very early stage of rheumatoid arthritis, affecting all metacarpo-phalangeal joints with loss of mineralization and discrete soft tissue swelling around the joints.
Figure 3:
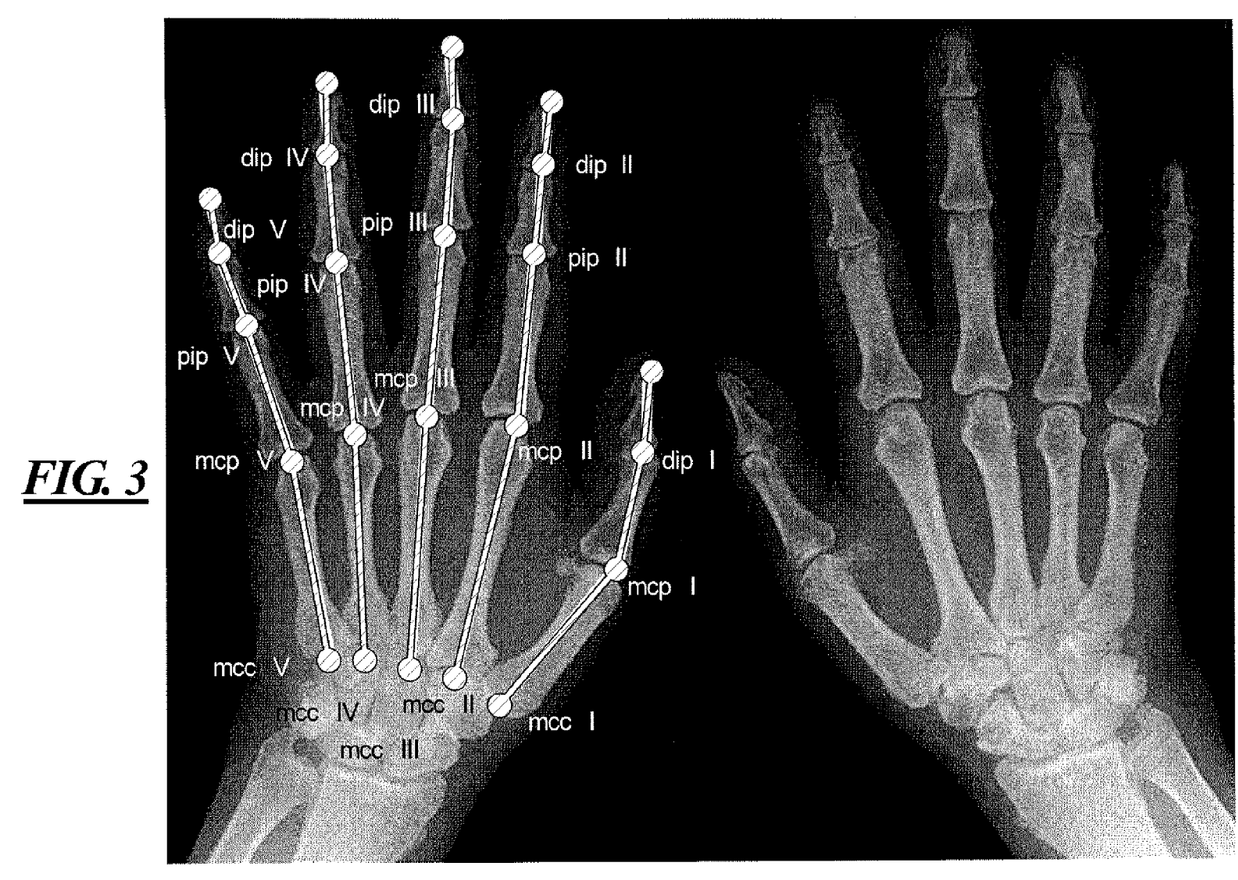
FIG. 3 is an example of the semi-automatic detection of different joint spaces of an extremity, again in the example of a hand, in accordance with the present invention.

A first embodiment of the invention begins with the acquisition of exposures of an extremity using different imaging modalities (steps 1 and 2 in FIG. 9), such as 2D x-ray, magnetic resonance, thermography, CT, scintigraphy or ultrasound. FIG. 2 shows such an exposure, in the example of an x-ray image of very early stage of rheumatoid arthritis. The arthritis affects all of the metacarpo-phalangeal joints, with a loss of mineralization and discrete soft tissue swelling around the joints. FIG. 3, as described in more detail below, shows the x-ray image of FIG. 2 that results after interaction of a user with the image of FIG. 2 in accordance with the present invention.

Figure 4A:
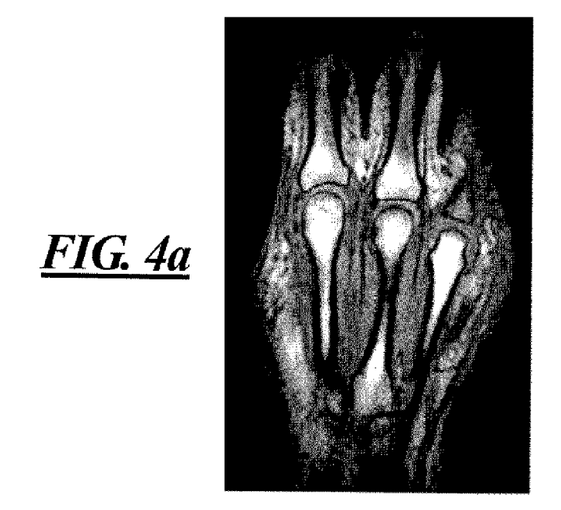
FIGS. 4a and 4b are magnetic resonance images, respectively before and after the administration of a contrast agent, of the hand of a patent exhibiting rheumatoid arthritis.
Figure 4B:
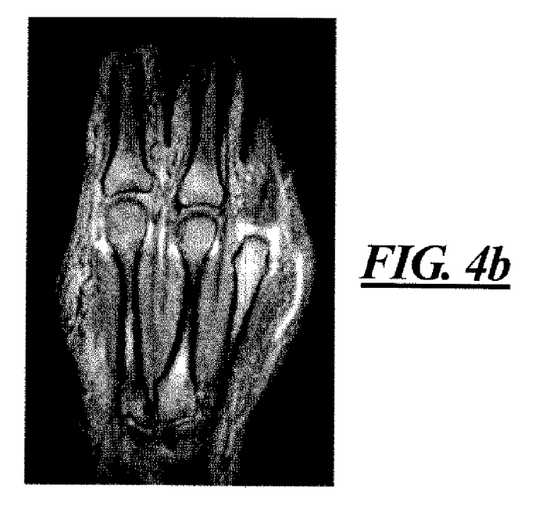
Figure 5A:
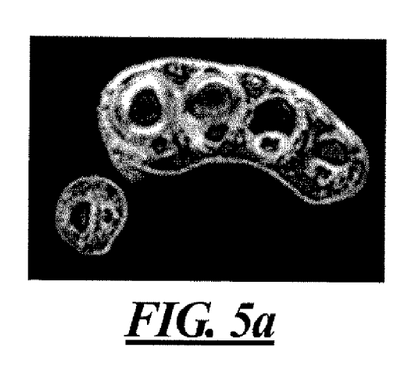
FIG. 5a is an MRI slice through the fingers and thumb of the hand of a patient exhibiting rheumatoid arthritis obtained with a FLASH-STIR sequence.
Figure 5B:
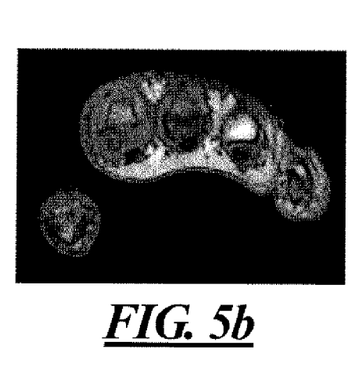
FIGS. 5b and 5c show the same section obtained with a gradient echo T1 weighted sequence, respectively before and after the administration of contrast agent.
Figure 5C:
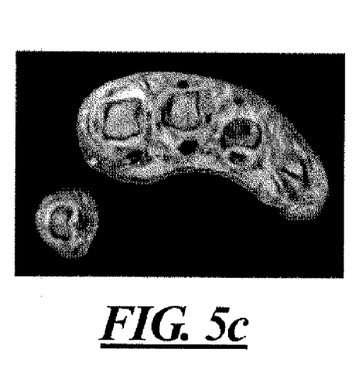

FIGS. 4a and 4b show exposures of the hand obtained by magnetic resonance using a T1-weighted gradient echo sequence. FIG. 4a is an exposure obtained before the administration of contrast agent, and FIG. 4b shows the same image after the administration of contrast agent. FIGS. 5a, 5b and 5c respectively show sectional views through the hand of a patient obtained by magnetic resonance imaging. FIG. 5a was obtained using a Flash-STIR sequence. FIGS. 5b and 5c were obtained with a T1-weighted gradient echo sequence, with FIG. 5b being obtained before the administration of contrast agent and FIG. 5c being obtained after the administration of contrast agent. One of these exposures obtained with one of the imaging modalities is automatically uploaded into a computer operating with an evaluation program in accordance with the invention (step 3 in FIG. 9). The computer may be a PACS or some other type of workstation.

Figure 9:
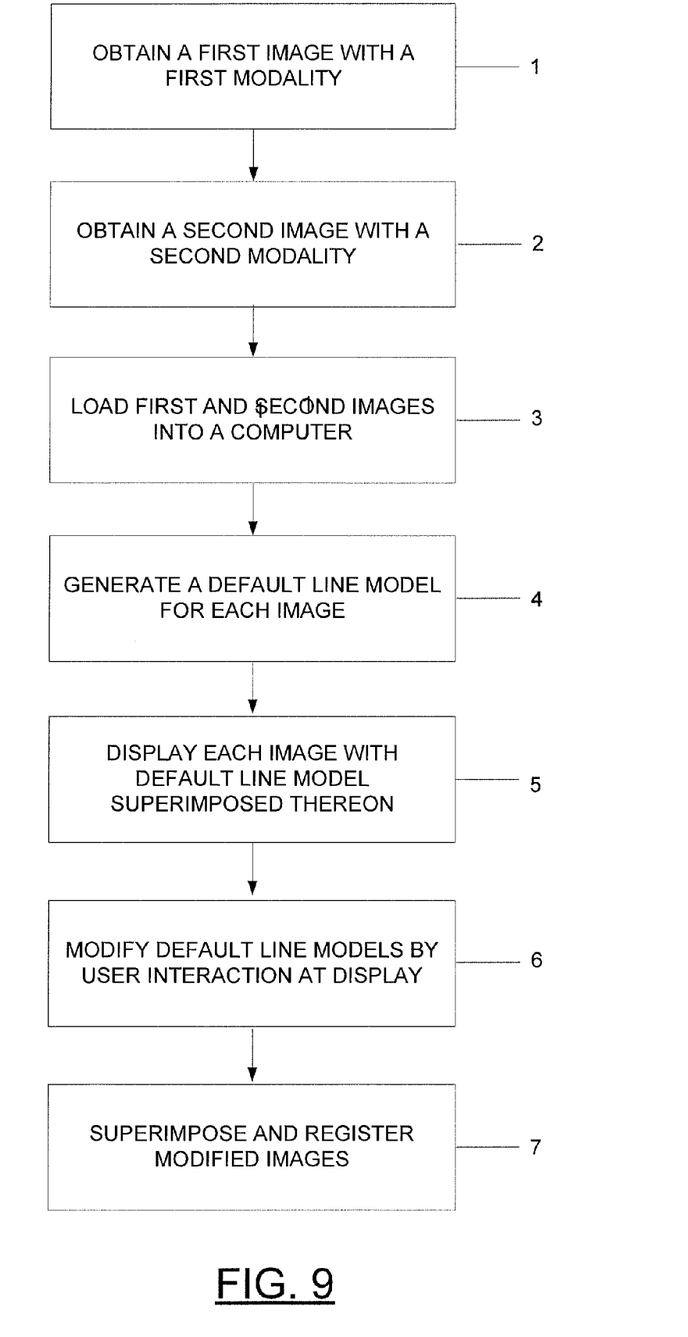
FIG. 9 is a flowchart showing the basic steps of an embodiment of the method according to the present invention.

The evaluation program provides the user, at a display of the computer, with a line model of one or both of the extremities (steps 4 and 5 in FIG. 9). The user interacts with the display to move a cursor to various characteristic structures of the displayed extremity, such as each individual joint or the carpal bones. The user then clicks on each of these characteristic structures. Such locations are indicated by the white circles in the example of FIG. 3, which is an example of such a display. The program automatically connects these indicated circles with lines, as also shown in FIG. 3. This procedure is implemented until each structure in the line model is completely adapted (step 6 in FIG. 9). Automatic contour recognition software is an alternative for implementing this procedure. The user can also provide labels for the respective characteristic structures. In the example of FIG. 3, the label DIP indicates distal interphalangeal joint, the designation PIP indicates proximal interphalangeal joint, and the designation MCC indicates metacarpo-carpal joint.

Upon completion of the modification, the user makes an entry that confirms that the adaptation is finished, and the evaluation program calculates the transformation from the initially displayed default line model into the adapted line model for each important indication in the model.

Figure 6A:
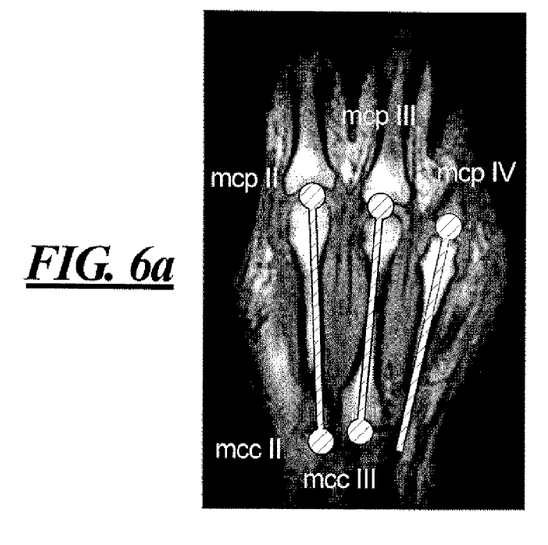
FIGS. 6a and 6b show FIGS. 4a and 4b, respectively, superimposed with the markers of FIG. 3, in accordance with the present invention.
Figure 6B:
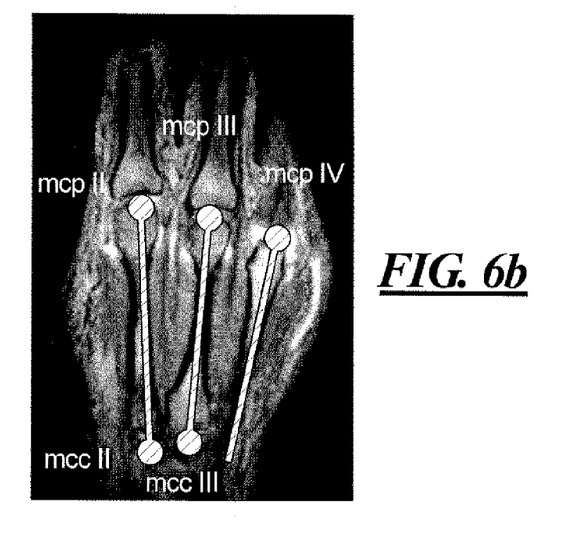
Figure 7A:
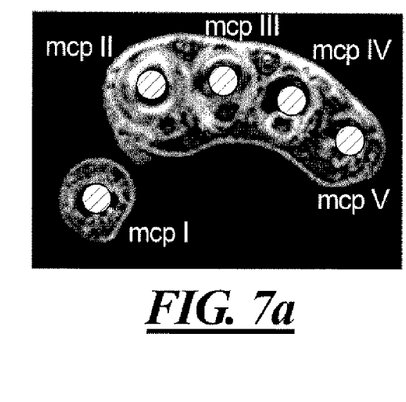
FIGS. 7a, 7b and 7c show FIGS. 5a, 5b and 5c, respectively, superimposed with the markers of FIG. 3 in accordance with the present invention.
Figure 7B:
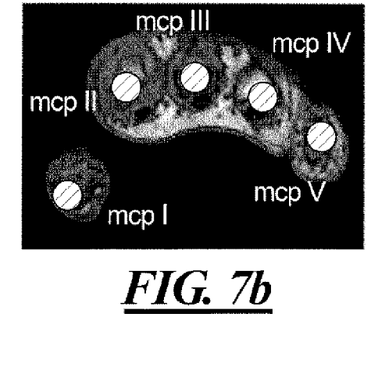
Figure 7C:
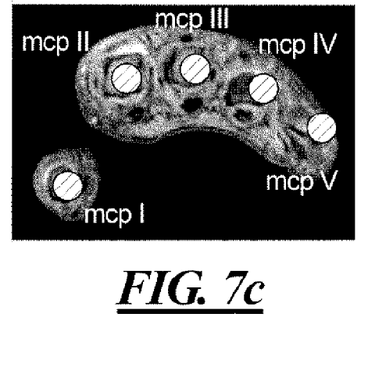

The above procedure is implemented for each exposure obtained with the respective, different imaging modalities. FIGS. 6a and 6b illustrate the result of such a procedure on the magnetic resonance images shown in FIGS. 4a and 4b, and FIGS. 7a, 7b and 7c illustrate the result of this procedure on the magnetic resonance images shown in FIGS. 5a, 5b and 5c.

Figure 8:
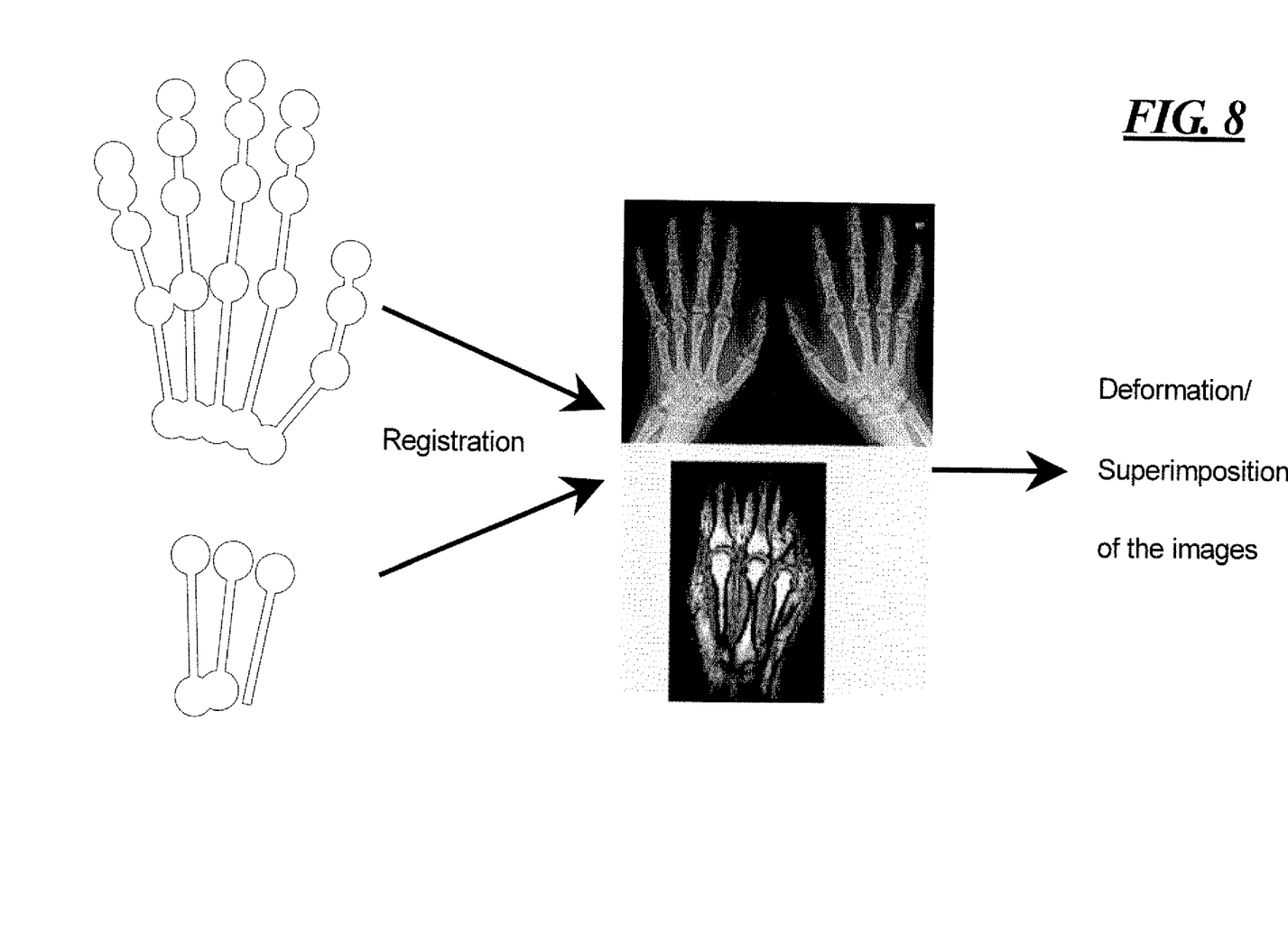
FIG. 8 schematically illustrates the co-registration of two different imaging modalities, namely x-ray and MRI in this example, with possible deformation, merged and overlaid with the markers in accordance with the present invention.

When all of these transformations have been calculated, all of the images can be registered together and can be superimposed, after a suitable deformation or scaling (step 7 in FIG. 9). This procedure is schematically illustrated in FIG. 8, in the examples of the aforementioned x-ray image of FIG. 2 and one of the magnetic resonance images of FIG. 5a or 5b (preferably the contrast agent-enhanced image of 5b).

Different color codings or transparent colors can be used in the superimposition. The user is also provided with the ability to select each individual image and to cause it to be displayed in the foreground. The user can also select the colors or the degree of transparency of the colors. The respective line models ensure accurate superimposition of the images. The superimposed (summation) image is then stored.

In view of the existing DICOM capability of all modalities, the user is also provided with the option of additionally superimposing images from subsequent examinations that were acquired using standard projections according to the aforementioned exposures.

In a further embodiment of the invention, ultrasound exposures, which may be in the form of images or cine loops of joints of an extremity, such as the hand joints, are registered together with images of the entire extremity, such as the entire hand, obtained with different imaging modalities such as the different imaging modalities mentioned above.

Each ultrasound image is provided with an anatomical designation in the DICOM header of the image, such as by using the designations noted above in FIG. 3 of the first embodiment.

At a computer with a display, such as a PACS or some other type of workstation, the images of the entire extremity are uploaded and a fusion or evaluation program corresponding to that described above is initiated. A line model of one or both extremities, in this case, one or both hands, is generated and adapted by the user in the manner described above, with the individual ultrasound exposures of the respective joints being provided with designations of the type described above. The program generates a concordance list between the adapted line model and the individual ultrasound exposures of the joints.

When a physician subsequently undertakes a medical diagnosis of the overall image, for example, an x-ray image of the hand, the user can then click on a selected joint. The corresponding ultrasound exposure of that joint is then automatically uploaded and displayed.

A significant advantage of both embodiments of the invention is the ability to accurately co-register images obtained with different modalities, thereby giving the user the benefit of the different imaging qualities associated with different types of imaging modalities. Moreover, functional information such as, for example, three-phase scintigraphy or ultrasound images, superimposed with the morphological anatomical detail information of an x-ray image can be obtained.

By having the ability to accurately to co-register (superimpose) images acquired using different imaging modalities, the ability to display soft tissue from a magnetic resonance image can be combined with the representation of bones, obtained from an x-ray image or a CT image. The invention also allows the superimposition of current exposures, pre-exposures and/or follow-up exposures, thereby allowing better assessment of the progression of arthritis/arthrosis.

The specific information from the different modalities is available to the radiologist or examining physician in a combination exposure. The individual modalities can be extracted and recombined at any time. The medical assessment of complex arthrotic/arthritic illnesses thus can be significantly simplified and standardized.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a diagnostic image of an anatomical extremity for diagnosing arthrosis/arthritis therein, comprising the steps of:
    obtaining a first image of an extremity with a first imaging modality and obtaining a second image of said extremity with a second imaging modality different from said first imaging modality;
    loading each of said first and second images into a computer having an associated display and, in succession for each of the loaded images, automatically generating in the computer a default line model of the extremity and automatically displaying the image at the display with said default line model superimposed thereon, and allowing manual adaptation of said default line model, by interaction with said display, to produce a modified line model conforming to anatomical details in the displayed image, resulting in said first image with a first modified line model superimposed thereon and said second image with a second modified line model superimposed thereon; and
    automatically in said computer, superimposing and co-registering said first image and said second image by conforming said first modified line model and said second modified line model with each other, to produce said diagnostic image.

2. A method as claimed in claim 1 comprising obtaining said first image using an imaging modality selected from the group consisting of two-dimensional x-ray imaging apparatuses, computed tomography apparatuses, magnetic resonance imaging apparatuses, ultrasound imaging apparatuses, scintigraphic imaging apparatuses, and thermographic imaging apparatuses.

3. A method as claimed in claim 1 comprising obtaining said second image using an imaging modality selected from the group consisting of two-dimensional x-ray imaging apparatuses, computed tomography apparatuses, magnetic resonance imaging apparatuses, ultrasound imaging apparatuses, scintigraphic imaging apparatuses, and thermographic imaging apparatuses.

4. A method as claimed in claim 1 wherein the step of modifying said default line model of said extremity comprises moving a cursor in the displayed image successively to a plurality of characteristic anatomical structures in the displayed image and making an entry into the compute when the cursor is at each of said characteristic structures, and connecting said characteristic structures with respective lines forming said modified line model.

5. A method as claimed in claim 4 comprising using respective joints in said extremity as said characteristic structures.

6. A method as claimed in claim 4 comprising using carpal bones in said extremity as said characteristic structures.

7. A method as claimed in claim 4 comprising using joints and carpal bones in said extremity as said characteristic structures.

8. A method as claimed in claim 4 comprising manually entering and displaying respective labels in the displayed image for said characteristic structures, and storing said labels in said computer with said displayed image and the modified line model.

9. A method for generating a diagnostic image of an anatomical extremity for diagnosing arthrosis/arthritis therein, comprising the steps of:
    loading into a computer a first image of an extremity obtained with a first imaging modality and a second image of said extremity obtained with a second imaging modality, different from said first imaging modality;
    in succession for each of the loaded images, automatically generating a default line model of the extremity in the computer and automatically displaying the image at a display associated with the computer, with said default line model superimposed thereon, and allowing manual adaptation of said default line model, by interaction with said display, to produce a modified line model conforming to anatomical details in the displayed image, resulting in said first image with a first modified line model superimposed thereon and said second image with a second modified line model superimposed thereon; and
    automatically in said computer, superimposing and co-registering said first image and said second image by conforming said first modified line model and said second modified line model with each other, to produce said diagnostic image.

10. A method as claimed in claim 9 wherein the step of modifying said default line model of said extremity comprises moving a cursor in the displayed image successively to a plurality of characteristic anatomical structures in the displayed image and making an entry into the computer when the cursor is at each of said characteristic structures, and connecting said characteristic structures with respective lines forming said modified line model.

11. A method as claimed in claim 10 comprising using respective joints in said extremity as said characteristic structures.

12. A method as claimed in claim 10 comprising using carpal bones in said extremity as said characteristic structures.

13. A method as claimed in claim 10 comprising using joints and carpal bones in said extremity as said characteristic structures.

14. A method as claimed in claim 10 comprising manually entering and displaying respective labels in the displayed image for said characteristic structures, and storing said labels in said computer with said displayed image and the modified line model.

15. A computer-readable medium encoded with a data structure, said medium being loadable into a computer having stored therein a first image of an extremity obtained with a first imaging modality, and a second image of said extremity obtained with a second imaging modality different from said first imaging modality, said data structure programming said computer to generate a diagnostic image of an anatomical extremity for diagnosing arthrosis/arthritis therein by:
in succession for each of the loaded images, automatically generate a default line model of the extremity and automatically displaying the image at a display associated with the computer, with said default line model superimposed thereon, and allowing manual adaptation of said default line model, by interaction with said display, to produce a modified line model conforming to anatomical details in the displayed image, resulting in said first image with a first modified line model superimposed thereon and said second image with a second modified line model superimposed thereon; and
automatically superimposing and co-registering said first image and said second image by conforming said first modified line model and said second modified line model with each other to produce said diagnostic image.

16. A method for generating a diagnostic image of an anatomical extremity for diagnosing arthrosis/arthritis therein, comprising:
obtaining a plurality of ultrasound images respectively of joints in an anatomical extremity of a subject;
to each of said ultrasound images, adding an electronic designation identifying an anatomical location of the joint shown in the respective ultrasound image;
obtaining an image of an entirety of said extremity;
loading the respective ultrasound images, with said electronic designations, and said image of the entirety of the extremity, into a computer and, in said computer, automatically displaying said image of the entirety of the extremity, as displayed image, and generating a default line model of said entirety of said extremity and superimposing said default line model in said displayed image, said line model comprising respective model elements at least approximately positioned at the respective anatomical locations identified by said electronic designations, and electronically linking the respective model elements to the respective ultrasound images via said locations, thereby generating said diagnostic image; and
displaying said diagnostic image and allowing user interaction therewith at a display by moving a cursor to any of said model elements in the diagnostic image and making an entry to display the ultrasound image of the joint at the anatomical position linked to the model element.

17. A method as claimed in claim 16 comprising allowing user interaction with the displayed line model superimposed on the displayed image of the entirety of the extremity, to modify said line model together with modifying locations respective positions of said model elements linked to said anatomical locations.

18. A method as claimed in claim 16 comprising generating said plurality of ultrasound images as a plurality of DICOM images, each having a header, and making said electronic designation identifying said anatomical location in said header.

19. A method as claimed in claim 16 comprising generating said image of said entirety of said extremity using an imaging modality selected from the group consisting of two-dimensional x-ray imaging apparatuses, computed tomography apparatuses, magnetic resonance imaging apparatuses, ultrasound imaging apparatuses, scintigraphic imaging apparatuses and thermographic imaging apparatuses.

20. A method for generating a diagnostic image of an anatomical extremity for diagnosing arthrosis/arthritis therein, comprising:
at a computer in which are stored a plurality of ultrasound images respectively of joints in an anatomical extremity of a subject, and an image of an entirety of said extremity, each of said ultrasound images having an electronic designation added thereto that identifies an anatomical location of the joint shown in the respective ultrasound image, automatically displaying said image of the entirety of the extremity and generating a default line model of said entirety of said extremity and superimposing said default line model in said image at said display, said line model comprising respective model elements at least approximately positioned at the respective anatomical locations identified by said electronic designations, and electronically linking the respective model elements to the respective ultrasound images via said locations, thereby generating said diagnostic image; and
displaying said diagnostic image and allowing user interaction therewith at a display by moving a cursor to any of said model elements in the diagnostic image and making an entry to display the ultrasound image of the joint at the anatomical position linked to the model element.

21. A method as claimed in claim 20 comprising allowing user interaction with the displayed line model superimposed on the image of the entirety of the extremity to modify said line model together with modifying locations respective positions of said model elements linked to said anatomical locations.

22. A computer-readable medium encoded with a data structure, said medium being loadable into a computer in which are stored a plurality of ultrasound images respectively of joints in an anatomical extremity of a subject, and an image of an entirety of said extremity, each of said ultrasound having an electronic designation added thereto that identifies an anatomical location of the joint shown in the respective ultrasound image; said data structure programming said computer to a diagnostic image of an anatomical extremity for diagnosing arthrosis/arthritis by:
automatically displaying said image of the entirety of the extremity and generating a default line model of said entirety of said extremity and superimposing said default line model in said image at said display, said line model comprising respective model elements at least approximately positioned at the respective anatomical locations identified by said electronic designations, and electronically linking the respective model elements to the respective ultrasound images via said locations, thereby generating said diagnostic image; and displaying said diagnostic image and allowing user interaction therewith at a display by moving a cursor to any of said model elements in the diagnostic image and making an entry to display the ultrasound image of the joint at the anatomical position linked to the model element.

* * * * *